(12) United States Patent
Kampinga et al.

(10) Patent No.: US 6,632,648 B1
(45) Date of Patent: *Oct. 14, 2003

(54) METHODS OF TERMINAL STERILIZATION OF FIBRINOGEN

(75) Inventors: Jaap Kampinga, Groningen (NL); Robert A. Alcock, Cambridgeshire (GB)

(73) Assignee: Elan Drug Delivery Limited, Nottingham (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/647,515

(22) Filed: May 14, 1996

(51) Int. Cl.[7] .................. C12N 7/04; A01N 37/18; A61K 38/00; A61K 35/14
(52) U.S. Cl. .................. 435/236; 514/2; 514/21; 530/382
(58) Field of Search .................. 435/236; 424/141.1, 424/1.11, 198.1, 278.1, 281.1; 514/2, 53, 177, 178, 182, 282, 535; 530/351, 363, 380, 381, 382, 383, 384, 386, 387.1, 393, 399

(56) References Cited

U.S. PATENT DOCUMENTS

| | | | |
|---|---|---|---|
| 3,557,717 A | 1/1971 | Chivers | 426/660 |
| 3,619,294 A | 11/1971 | Black et al. | 127/30 |
| 3,632,357 A | 1/1972 | Childs | 426/660 |
| 3,655,442 A | 4/1972 | Schwer et al. | 127/58 |
| 4,127,502 A | 11/1978 | Li Mutti et al. | 436/16 |
| 4,158,544 A | 6/1979 | Louderback | 436/16 |
| 4,294,826 A | 10/1981 | Feldman | 530/383 |
| 4,327,076 A | 4/1982 | Puglia et al. | 424/441 |
| 4,327,077 A | 4/1982 | Puglia et al. | 424/441 |
| 4,402,950 A | 9/1983 | Wolf et al. | 424/195.1 |
| 4,424,206 A | 1/1984 | Ohmura et al. | 530/390.1 |
| 4,440,679 A * | 4/1984 | Fernandes et al. | 530/363 |
| 4,456,590 A | 6/1984 | Rubinstein | 514/2 |
| 4,490,361 A | 12/1984 | Heldebrant | 530/383 |
| 4,588,744 A | 5/1986 | McHugh | 514/470 |
| 4,640,834 A | 2/1987 | Eibl et al. | 424/176.1 |
| 4,677,195 A | 6/1987 | Hewick et al. | 514/8 |
| 4,684,719 A | 8/1987 | Nishikawa et al. | 536/119 |
| 4,701,417 A | 10/1987 | Portenhauser et al. | 436/13 |
| 4,749,783 A | 6/1988 | Jordan et al. | 530/393 |
| 4,758,657 A | 7/1988 | Farb et al. | 530/383 |
| 4,762,857 A | 8/1988 | Bollin, Jr. et al. | 514/777 |
| 4,789,389 A | 12/1988 | Winkelman | 530/383 |
| 4,793,997 A | 12/1988 | Drake et al. | 424/426 |
| 4,814,436 A | 3/1989 | Shibata et al. | 536/17.1 |
| 4,865,871 A | 9/1989 | Livesey et al. | 435/1.3 |
| 4,879,280 A | 11/1989 | Seyffart et al. | 514/53 |
| 4,883,762 A | 11/1989 | Hoskins | 436/18 |
| 4,891,319 A | 1/1990 | Roser | 435/188 |
| 4,909,940 A | 3/1990 | Horowitz et al. | 210/634 |
| 4,994,438 A | 2/1991 | Rubinstein | 514/2 |
| 5,026,566 A | 6/1991 | Roser | 426/443 |
| 5,097,018 A | 3/1992 | Rubinstein | 530/383 |
| 5,099,002 A | 3/1992 | Rubinstein | 530/381 |
| 5,118,795 A * | 6/1992 | Rubinstein | 530/383 |
| 5,132,406 A | 7/1992 | Uemura et al. | 530/390.1 |
| 5,149,653 A | 9/1992 | Roser | 435/260 |
| 5,192,743 A | 3/1993 | Hsu et al. | 514/8 |
| 5,290,765 A | 3/1994 | Wettlaufer et al. | 514/23 |
| 5,306,506 A | 4/1994 | Zema et al. | 424/466 |
| 5,348,852 A | 9/1994 | Bonderman | 435/4 |
| 5,418,130 A | 5/1995 | Platz et al. | 435/2 |
| 5,422,384 A | 6/1995 | Samuels et al. | 523/170 |
| 5,425,951 A | 6/1995 | Goodrich, Jr. et al. | 424/520 |
| 5,512,547 A | 4/1996 | Johnson et al. | 514/21 |
| 5,589,167 A | 12/1996 | Cleland et al. | 424/85.7 |

FOREIGN PATENT DOCUMENTS

| | | | |
|---|---|---|---|
| EP | 0094611 | 11/1983 | |
| EP | 0177685 | 4/1986 | A61L/4/04 |
| EP | 0212040 | 3/1987 | A61L/2/00 |
| EP | 02610332 | 3/1988 | A61L/2/20 |
| EP | 012044 | 9/1990 | A61L/2/04 |
| EP | 0415567 | 3/1991 | |
| EP | 0399321 | 6/1993 | A61K/35/16 |
| EP | 0217662 | 1/1994 | A61L/2/12 |
| EP | 0295940 | 3/1994 | C12N/9/72 |
| EP | 0600730 | 6/1994 | B01J/20/22 |
| EP | 0699687 | 3/1996 | C07K/14/765 |
| EP | 0714905 | 6/1996 | |
| GB | 1381588 | 1/1975 | |
| GB | 2206273 | 1/1989 | |
| JP | 58-216695 | 12/1983 | |
| JP | 63-502592 | 9/1988 | |
| JP | 6-70718 | 3/1994 | A23L/1/30 |
| NL | 8700484 | 9/1988 | A61J/37/02 |
| WO | WO 87/00196 | 1/1987 | |
| WO | WO 89/06542 | 7/1989 | |

(List continued on next page.)

OTHER PUBLICATIONS

Gibco BRL Life Technologies Catalog, p. 6–34, 1993.*

(List continued on next page.)

Primary Examiner—Sandra E. Saucier
(74) Attorney, Agent, or Firm—Morrison & Foerster LLP

(57) ABSTRACT

The invention relates to methods of sterilizing biologically active products, particularly therapeutic or prophylactic products and the compositions obtained thereby. The methods include obtaining a dried sample containing an amount of trehalose sufficient to render heat stability to the product and exposing the dried sample to heating conditions at a temperature and for a duration sufficient to substantially inactivate viruses, especially non-lipid encapsulated viruses. The drying methods include both ambient drying conditions and lyophilization. The heating conditions include any known in the art and cover a wide range of temperatures and heating times. The compositions obtained contain stable products and do not contain measurable infectious virus, particularly parvovirus.

26 Claims, No Drawings

FOREIGN PATENT DOCUMENTS

| WO | WO 90/11756 | 10/1990 |
|----|-------------|---------|
| WO | WO 92/02133 | 2/1992 |
| WO | WO 93/02834 | 2/1993 |
| WO | WO 93/10758 | 6/1993 |
| WO | WO 93/11220 | 6/1993 |
| WO | 93/23065 | * 11/1993 |
| WO | WO 95/06126 | 3/1995 |
| WO | WO 95/33488 | 12/1995 |

OTHER PUBLICATIONS

The Merck Index, Tenth Edition, Merck & Co., Inc., Rahway, NJ, pp. 207, 898, 899, 1312, 1313, and 1420, 1983.*

Dialog® English Abstract of JP 58–216695 (Dec. 16, 1983).

Dialog® English Abstract of JP 63–502592 (Sep. 29, 1988).

Sakuri, Y. (ed.), "Food General Dictionary" Sixth Edition, (English translation is 10 pages total).

Kanna et al., "Denaturation of Fish Muscle Protein by Dehydration—V." Bull. Tokai Reg. Fish. Res. Lab. (1974) 77:1–17.

Derwent® WPI File 351 Abstract of PCT WO 87/05300 (Sep. 11, 1987).

Derwent® WPI Abstract of JP 8298125 (Jun. 7, 1982).

Handbook of Natural Materials for Food Processing, Ninth Edition, pp. 384 and 495.

Chemical Dictionary, 7$^{th}$ Edition, pp. 310–311.

*Stability and characterization of protein and peptide drugs*, Wang et al. (eds.), 1993, Table of contents.

Cuthbertson et al., "Viral contamination of human plasma and procedures for preventing virus transmission by plasma products" Blood Separation and Plasma Fractionation, Wiley–Liss, Inc. (1991) pp. 385–435.

Mozen, "HIV inactivation in plasma products" J. Clin. Apheresis (1993) 8:126–130.

Ingerslev, "Safety of plasma derivatives" Haemostasis (1994) 24:311–323.

Dorner et al., "At what stage should virus inactivation be carried out?" Virological Safety Aspects of Plasma Derivatives. Dev. Biol. Stand., Brown, F., ed., Basel, Karger (1993) 81:137–143.

Mannucci, "Clinical evaluation of viral safety of coagulation factor VIII and IX concentrates" Vox Sang. (1993) 64:197–203.

Hamman et al., "Removal and inactivation of hepatitis A virus (HAV) during processing of factor VIII concentrates" Vox Sang. (1994) 67:72–77.

Grandgeorge et al., "Viral validation of the manufacturing process of high purity albumin from placentas" Virological Safety Aspects of Plasma Derivatives. Dev. Biol. Stand., Brown, F., ed., Basel, Karger (1993) 81:237–244.

Erickson, "Life in the blood" Sci. Am. (Feb. 1991) pp. 126–127.

Colvin et al., "Effect of dry–heating of coagulation factor concentrates at 80° C for 72 hours on transmission of non–A, non–B hepatitis" Lancet (Oct. 8, 1988) pp. 813–816.

Sherwood, "The significance of the blood–borne viruses: Blood banking and transfusion medicine" Virological Safety Aspects of Plasma Derivatives. Dev. Biol. Stand., Brown, F., ed., Basel, Karger (1993) 81:25–33.

Barrowcliffe, "Viral inactivation vs. biological activity" Virological Safety Aspects of Plasma Derivatives. Dev. Biol. Stand., Brown, F., ed., Basel, Karger (1993) 81:125–135.

Cossart et al., "Parvovirus–like particles in human sera" Lancet (Jan. 11, 1975) pp. 72–73.

Williams et al., "Transmission of human parvovirus B19 by coagulation factor concentrates" Vox Sang. (1990) 58:177–181.

Corsi et al., "Human parvovirus infection in heamophiliacs first infused with treated clotting factor concentrates" J. Med. Virol. (1988) 25:165–170.

Soumela, "Inactivation of viruses in blood and plasma products" Trans. Med. Rev. (1993) VII:42–57.

Nowak et al., "Inactivation of HIV, HBV, HCV related viruses and other viruses in human plasma derivatives by pasteurisation" Virological Safety Aspects of Plasma Derivatives. Dev. Biol. Stand., Brown, F., ed., Basel, Karger (1993) 81:169–176.

Knevelman et al., "Development and small–scale production of a severely heated factor VIII concentrate" Vox Sang. (1994) 66:89–95.

Santagostino et al., "Eliminating parvovirus B19 from blood products" Lancet (Mar. 26, 1994) 343:798.

Yee et al., "Life–threatening human parvovirus B19 infection in immunocompetent haemophilia" Lancet (Mar. 25, 1995) 345:794–795.

Wieding et al., "Inactivation of viruses in fresh–frozen plasma" Ann. Hematol. (1993) 67:259–266.

Horowitz et al., "Viral safety of solvent–detergent treated blood products" Virological Safety Aspects of Plasma Derivatives. Dev. Biol. Stand., Brown, F., ed., Basel, Karger (1993) 81:147–161.

Isaacs et al., "Inactivation of enveloped viruses in human bodily fluids by purified lipids$^{a}$" Ann. NY Acad. Sci. (1994) 724:457–464.

Lawrence, "Affinity chromatography to remove viruses during preparation of plasma derivatives" Virological Safety Aspects of Plasma Derivatives. Dev. Biol. Stand., Brown, F., ed., Basel, Karger (1993) 81:191–197.

Teh, "Preparation of intermediate–purity factor VIII concentrate by direct gel filtration of cryoprecipitate" Vox Sang. (1993) 65:251–257.

Lebing et al., "A highly purified antithrombin III concentrate prepared from human plasma fraction IV–1 by affinity chromatography"Vox Sang. (1994) 67:117–124.

DiScipio, "The fractionation of human plasma proteins. III. Purification of complement factors D and I using affinity chromatography" Prot. Exp. Purif. (1994) 5:178–186.

Morgenthaler et al., "Partitioning and inactivation of viruses during isolation of albumin and immunoglobulins by cold ethanol fractionation" Virological Safety Aspects of Plasma Derivatives. Dev. Biol. Stand., Brown, F., ed., Basel, Karger (1993) 81:185–190.

Erickson, "The hole story. Fine–pore membranes remove viruses from biological drugs" Sci. Am. (Sep. 1992) pp. 163–164.

McCreath et al., "Novel affinity separations based on perfluorocarbon emulsions. Development of a perfluorocarbon emulsion reactor for continuous affinity separations and its application in the purification of human serum albumin from blood plasma" J. Chromatog. (1993) 629:201–213.

Hilfenhaus et al., "Theoretical and technical concerns in inactivation/elimination of viruses in plasma derivatives" Virological Safety Aspects of Plasma Derivatives. Dev. Biol. Stand., Brown, F., ed., Basel, Karger (1993) 81:117–123.

Blakeley et al., "Dry instant blood typing plate for bedside use" Lancet (Oct. 6, 1990) pp. 854–855.

Roser et al., "Trehalose, a new approach to premium dried foods" *Trends in Food Sci and Tech.* (Jul. 1991) pp. 166–169.

Colaco, "Trehalose stabilisation of biological molecules" *Biotechnol. Internat.* (1992) pp. 345–350.

Roser, "Trehalose drying: A novel replacement for freeze–drying" *BioPharm.* (Sep. 1991) 4:47–53.

Colaco et al., "Extraordinary stability of enzymes dried in trehalose: Simplified molecular biology" *Bio/Technol.* (1992) 10:1007–1011.

Roser et al., "A sweeter way to fresher food" *New Scientist* (1993) pp. 25–28.

Madzarovova–Nohejlova, "Trehalase deficiency in a family" *Gastroenterol.* (1973) 65:130–133.

Ravich et al., "Carbohydrate absorption and malabsorption" *Clin. Gast.* (1983) 12:335–356.

Sacktor, "Trehalase and the transport of glucose in the mammalian kidney and intestine" *Proc. Natl. Acad. Sci. USA* (1968) 60:1007–1014.

Belfiore et al., "Serum enzymes in diabetes mellitus" *Clin. Chem.* (1973) 19:447–452.

Eze, "Plasma trehalase activity and diabetes mellitus" *Biochem. Genet.* (1989) 27:487–495.

Yoshida et al., "Serum trehalase activity in patients with rheumatoid arthritis" *Clin. Chim. Acta* (1993) 215:123–124.

Kramers et al., "Cell membrane enzymes: L–γ–glutamyl transpeptidase, leucine aminopeptidase, maltase and trehalase in normal and leukaemic lymphocytes" *Brit. J. Haematol.* (1978) 38:453–461.

Bergoz et al., "Significance of duodenal disaccharidases. A comparative study of duodenal and jejunal values" *Digestion* (1981) 22:108–112.

Riby et al., "Rat intestinal brush border membrane trehalase: Some properties of the purified enzyme" *Comp. Biochem. Physiol.* (1985) 82B:821–827.

Chen et al., "Rat intestinal trehalase" *Biochem. J.* (1987) 247:715–724.

Bhattacharya et al., "Elimination of virus from high purity FVIII product" *XXI International Congress of the World Federation of Hemophilia*, (Apr. 24–29, 1994), Mexico, D. F. (abstract).

Burnouf, "Chromatographic removal of viruses from plasma derivatives" *Virological Safety Aspects of Plasma Derivatives. Dev. Biol. Stand.*, Brown, F., ed.,. Basel, Karger, (1993) 81:199–209.

Burnouf, "New trends in plasma fractionation and plasma products. Trends in plasma fractionation" *Vox Sang.* (Jul. 1994) Title page; Table of Contents; pp. 251–253.

Ford et al., "The effect of carbohydrate additives in the freeze–drying of alkaline phosphatase" *J. Pharm. Pharmacol.* (1993) 45:86–93.

Fox, "Putting proteins under glass" *Science* (1995) 267:1922–1923.

Jensen et al., "Identification and removal of polymer– and aggregate– forming proteins in human plasma albumin preparations" *Vox Sang.* (1994) 67:125–131.

Kaplan et al., "Current status of solvent/detergent treated plasma" *News Briefs* (Oct. 1993) pp. 12–13.

Reid, "Gamma processing technology: An alternative technology for terminal sterilization of parenterals" PDA J. Pharm. Sci. & Tech. (Mar.–Apr. 1995) 49:83–89.

Shapiro, "Blood banking—vapor heated viral inactivation" *Blood Weekly* (Apr. 17, 1995) pp. 22–23.

Cicardi et al., "Blood banking—viral inactivation" *Blood Weekly* (Apr. 17, 1995) pp. 23.

Vyas, "Inactivation and removal of blood–borne viruses" *Transfusion* (May 1995) 35:367–370.

\* cited by examiner

METHODS OF TERMINAL STERILIZATION OF FIBRINOGEN

TECHNICAL FIELD

This invention relates to the field of sterilization of products derived from blood and other biological sources. The invention involves heating biologically active products in the presence of trehalose for a time and under conditions sufficient to kill viruses, particularly parvovirus.

BACKGROUND ART

The complete removal of viruses and other contaminants from biologically active products is essential to the production and use of a wide variety of therapeutic and prophylactic products. A number of methods are currently being used. Primarily, these are dry heat treatment, chromatography, solvent-detergent (SD) treatment and pasteurization. These methods all suffer from drawbacks and none has been successful in eliminating all known viruses. There may also be viruses that have not yet been characterized that are not inactivated by these methods. For review, see Cuthbertson et al. (1991) *Blood Separation and Plasma Fractionation*, Wiley-Liss, Inc. pp. 385–435; Mozen (1993) *J. Clin. Apheresis* 8:126–130; Ingerslev (1994) *Haemostasis* 24:311–323; Dorner et al. (1993) *Virological Safety Aspects of Plasma Derivatives*, Brown, ed., Dev. Biol. Stand., Basel, Karger, vol. 81, pp. 137–143; Mannucci (1993) Vox Sang. 64:197–203; and Hamman et al. (1 994) Vox Sang. 67:72–77.

A wide variety of products with therapeutic utility are derived from biological sources such as plasma and cell lines. Most of the plasma used for fractionation in the United States is obtained by plasmapheresis at collection centers distributed across the country. The centers provide plasma to commercial fractionators in the United States and Europe. About 9 million liters of plasma are collected per year from about 13 million donations. The Red Cross adds approximately 800,000 liters to this number.

Products from human plasma may be classified into several groups: the albumin products; the immune globulins; the cold insoluble globulins; the coagulation products; and the protease inhibitors. The albumin products, also termed fraction V products, are used primarily to restore colloidal osmotic pressure in conditions of shock such as burn, or hemorrhagic shock where fluid loss is a principal problem.

The immune globulins, or "gamma globulins," are isolated from fraction II and contain a mixture of antibodies representative of the plasma pool source. A number of hyperimmune globulins used for passive immunization are isolated from donor plasma with high levels of protective antibody. The cold insoluble globulins include fibrinogen and von Willebrand's factor.

The coagulation products include the antihemophilic factor VIII and factor IX complex used for replacement therapy in hemophilia A and B, respectively. An activated form of factor IX complex called anti-inhibitor coagulant complex is prepared and used for treating patients with a factor VIII inhibitor. The protease inhibitors include α-1-proteinase inhibitor, also known as α-1-anti-trypsin which is used to treat a congenital deficiency. Antithrombin III is an inhibitor that is also congenitally deficient leading to thrombotic complications.

Other body fluids are the source of therapeutic products. For instance, erythropoietin was previously purified from the blood or urine of aplastic anemia patients. U.S. Pat. No. 4,677,195. High purity albumin has also been obtained from human placentas. Grandgeorge and Veron (1993) *Virological Safety Aspects of Plasma Derivatives*, Brown, ed. Dev. Biol. Stand. Basel, Karger, vol. 81, pp. 237–244. The production of recombinant proteins in the milk of transgenic animals is now a commercial reality.

Numerous therapeutic products are now obtained from cell cultures expressing recombinant proteins. The cell cultures are routinely grown in the presence of animal or human serum. The products are obtained from the cells or from the cell culture supernatant and thus may contain viruses, either from the media or the cells themselves. These products obtained include, but are not limited to, colony stimulating factors, monoclonal antibodies and derivatives thereof, growth factors such as erythropoietin, interleukins. Growth factors alone represent a multimillion dollar industry. For review, see, Erickson (1991) *Sci. Am.*, February 1991 pp. 126–127.

Although the risk of viral contamination of proteins derived from cell culture is much less than that associated with plasma products, there is always the risk of viral contamination when dealing with cells. For this reason, products such as monoclonal antibodies are subject to heat treatment in order to inactivate viruses. Furthermore, the addition of human serum albumin (HSA) to stabilize formulations of recombinant proteins is common practice.

The major blood-borne viruses of clinical concern include the hepatitis B and C viruses and the HIV and HTLV retroviruses. With respect to blood derivatives, HTL VI and II and cytomegalovirus (CMB) appear to be cell-associated and thus do not present a risk in cell-free products.

As new viruses are discovered, inactivation protocols are changed to accommodate them. For instance, the finding that the human immunodeficiency virus (HIV) survived standard processing of factor VIII necessitated a change of protocol requiring the addition of HSA to stabilize the product under the new, more severe, conditions. Mozen (1993).

Methods to inactivate HIV and the hepatitis viruses in plasma fractions are known. As described above, heating at 60° C. for 10 hours in the presence of HSA inactivates HIV. Non-A, non-B hepatitis (NANBH) was found to be inactivated in factor VIII and IX preparations by heating at 80° C. for 72 hours in the freeze dried state. Study group of the UK Haemophilia Centre, Directors on Surveillance of Virus Transmission by Concentrates (1988) *Lancet* October 8, pp. 814–816.

In recent years, a few transfusion-transmissible diseases have been identified that, although uncommon from the public health perspective, have both real and potential transfusion impacts for the use of plasma and plasma derivatives as well as cellular products. These include transmission of parvovirus (B19). This etiologic agent appears to be resistant to the current methods used for viral inactivation. Sherwood (1993) Brown, ed. *Virological Safety Aspects of Plasma Derivatives*, Dev. Biol. Stand. Basel, Karger vol. 81, pp. 25–33.

The virus inactivation methods currently in use may also cause changes in the biological activity of the biological products obtained. Immunogenicity of the products is especially of concern where sterilization treatment may induce protein unfolding and/or aggregation. For instance, it has been found that factor VIII concentrates display evidence of FVIII activation, with higher one-stage than two-stage potencies, more rapid FXa generation, and increased lower molecular weight polypeptides. Viral inactivation procedures may also induce changes in non-FVIII components and these may be partly responsible for the immunosuppressive activity of some of these concentrates. Barrowcliffe (1993) *Virological Safety Aspects of Plasma Derivatives* Brown, ed. Dev. Biol. Stand. Basel, Karger, vol. 81, pp. 125–135.

Notable changes in immune system functions both in vitro and ex vivo have been found in patients frequently exposed to biologically derived products. In HIV-negative patients, changes include decreased numbers and functions of immune competent cells as assessed by their response to stimuli and in terms of markers of their cellular turnover. These changes are likely to occur when chronic viral disease is present. Furthermore denatured allogeneic protein impurities of factor concentrates and other contaminants may also be responsible for immunosuppression. See, Ingerslev (1994) for review.

Human parvovirus is a recently discovered agent that was given the code name B19. Cossart et al. (1975) Lancet 1:72–73. It is a very small (24 nm) single-stranded DNA virus with a very simple protein coat, but no lipid outer envelope. It causes a transient viraemia of 1–2 weeks but can achieve extraordinarily high circulating virus titres of at least $10^{12}$ virus particles per ml. Although parvovirus normally causes a relatively minor illness that is frequently not clinically apparent, producing a mild rubella-like rash known as fifth disease or erythema infectiosum, it can also cause more severe reactions. Parvovirus infects bone marrow stem cells and this can cause a severe, life-threatening condition in patients with a preexisting, underlying anemia. Aplastic crisis as a result of acute interruption of haemopoiesis may occur in patients with congenital haemolytic anaemias and immuno-deficiency states. Parvovirus also causes hydrops fetalis in pregnant women. Thus parvovirus represents a danger of infection to those patients receiving plasma-derived therapeutic agents, particularly in those patients with haemostatic disorders. It is of concern that this virus is transmitted by some concentrates despite the use of robust virucidal methods and chromatographic removal, not only for the risk of transmission of parvovirus, but because other pathogenic viruses with the same features may exist.

A study of children with haemolytic disorders found that parvovirus is rapidly infectious in plasma derivatives that have not been heat-treated. In one study, a small group of children (N=9) treated with heat-treated factor VIII concentrate did not become infected with parvovirus. Williams et al. (1990) *Vox Sang.* 58:177–181. However, others have found heat-treated products do transmit parvovirus infection. Corsi et al. (1988) *J. Med. Virol.* 25:151–153. Unlike hepatitis and HIV, parvovirus is not tested for in individual plasma donations and thus is present in pooled plasma.

As mentioned above, various treatments have been proposed or are in use for inactivation of viruses in biologically-derived therapeutic products. For review, see Soumela (1993) *Trans. Med. Rev.* VII:42–57. The end product has been obtained by a combination of partition steps and inactivation steps, both of which serve to reduce the viral load.

There are several heat treatments currently in use. Heating in solution is commonly used for albumin products. This is otherwise known as pasteurization. Viruses are inactivated by heating the liquid samples for at least 10 hours at 60° C. in the presence of a small amount of stabilizer such as caprylate or tryptophanate. This method is unsuitable for other products, however, as most proteins denature under these conditions. Pasteurization has been shown to inactivate a wide spectrum of viruses including HIV, HBV, HCV, HAV, HSV, poliovirus CMV, mumps virus, measles virus and rubella virus. Nowak et al. (1993) *Virological Safety Aspects of Plasma Derivatives*, Brown, ed., Dev. Biol. Stand. Basel, Karger, vol. 81, pp. 169–176; and Soumela (1993). In these studies, parvovirus was not tested for. Further, the use of pasteurized coagulation factors has been associated with the formation of neoantigens. Ingerslev (1994).

Heating of dry products is performed when freeze-dried, labile proteins tolerate temperatures up to 68° C. Earlier methods that included heating at 60° C. were used to inactivate hepatitis viruses. See, e.g., U.S. Pat. No. 4,456,590. However, these conditions were insufficient to inactivate HIV as evidenced by transmission of the virus through purified coagulation factors. Products treated at 68° C. for 72 hours were also found to be unsafe. Soumela (1993). More recently, higher temperatures and longer heating times, such as 80° C. for 72 hours have been used to ensure inactivation of hepatitis viruses and HIV. See, e.g., Knevelman et al. (1994) *Vox Sang.* 66:89–95. However, most labile biological actives, especially biopharmaceuticals do not survive exposure to such extreme temperature/time conditions. Another drawback of this method is the often unpredictable result with regard to the inactivation of parvovirus. Santagostino et al. (1994) *Lancet* 343:798; and Yee et al. (1995) *Lancet* 345:794.

Solvent/Detergent (SD) inactivation of viruses relies on the disruption of the membranes of viruses that have lipid envelopes. The viruses are rendered non-infectious either by structural disruption or destruction of the cell receptor recognition site. Although most human pathogenic viruses have a lipid envelope, parvovirus and HAV do not and are not inactivated by this method. For review, see, Wieding et al. (1993) *Ann. Hematol.* 67:259–266. The SD method is in use in numerous countries. Horowitz et al. (1993) *Virological Safety Aspects of Plasma Derivatives*; Brown, ed. Dev. Biol. Stand. Basel, Karger, vol. 81, pp. 147–161. In a related method, lipids have been used to inactivate viruses with lipid envelopes. Isaacs et al. (1994) *Ann. NY Acad. Sci.* 724:457–464.

A number of other methods have been developed or are under development. For instance, cold sterilization of plasma is performed by exposing plasma to a combination of β-propiolactone and UV light. However, this method reduces the activity of labile proteins. Various chemical treatments have been proposed including the use of psoralens and UVA, BPD-MA and light, although these may be limited to inactivation of lipid-enveloped viruses. Caprylate and sodium chlorite have also been found to be virucidal. Various physical separation methods have been tested including affinity chromatography; cold ethanol fractionation, fine-pore membranes, and perfluorocarbon emulsions. Lawrence (1993) *Virological Safety Aspects of Plasma Derivatives*, Brown, ed., Dev. Biol. Stand. Basel, Karger, vol. 81, pp. 191–197; Burnouf (1993) id., pp. 199–209; (1993) *Vox Sang.* 65:251–257; Lebing et al. (1994) *Vox Sang.* 67:117–124; DiScipio (1994) *Prot. Exp. Purif.* 5:178–186; Morgenthaler and Omar (1993) *Virological Safety Aspects of Plasma Derivatives*, Brown, ed., vol. 81, pp. 185–190; Erickson (1992) *Sci. Am.* September pp. 163–164; and McCreath et al. (1993) *J. Chromatog.* 629:201–213.

Determination of successful virus inactivation during manufacture of a plasma protein requires that three prerequisites are fulfilled. First, the manufacturing procedure must be scaled down as exactly as possible. Second, the relevant test viruses must be selected for the spiking experiments. Third, the resulting samples must be assayed properly for infectious virus. The process of such testing is described in detail for instance by Hilfenhaus et al. (1993) Brown, ed. *Virological Safety Aspects of Plasma Derivatives* Dev. Biol. Stand. Basel, Karger vol. 81 pp. 117–123. These guidelines have been followed herein.

Trehalose, (α-D-glucopyranosyl-α-D-glucopyranoside), is a naturally occurring, non-reducing disaccharide which was initially found to be associated with the prevention of desiccation damage in certain plants and animals which can dry out without damage and can revive when rehydrated. Trehalose is available commercially in the dihydrate form. Trehalose has been shown to be useful in preventing denaturation of proteins, viruses and foodstuffs during desiccation. See U.S. Pat. Nos. 4,891,319; 5,149,653; 5,026,566; Blakeley et al. (1990) *Lancet* 336:854–855; Roser (July 1991) *Trends in Food Sci. and Tech.* 166–169; Colaco et al. (1992) *Biotechnol. Internat.* 345–350; Roser (1991) *BioPharm.* 4:47–53; Colaco et al. (1992) *Bio/Tech.* 10:1007–1011; and Roser et al. (May 1993) *New Scientist*, pp. 25–28. Trehalose dihydrate is available in good manufacturing process (GMP) grade crystalline formulations. A method of making a desiccant, anhydrous form of trehalose is described in EP patent publication no. 600 730. This method involves heating a trehalose syrup in the presence of a seed crystal and recovering the anhydrous trehalose.

Trehalose is found extensively in such diverse animal and plant species as bacteria, yeast, fungi, insects and invertebrates. In many insects, it is the major blood sugar. The only major source for man is dietary in foods such as mushrooms and yeast products. Madsarovova-Nohejlova (1973) *Gastroenterol.* 65:130–133.

Trehalose is described for use in a peritoneal dialysis system in U.S. Pat. No. 4,879,280 where it is mentioned as one of several disaccharides as a replacement for the prior art system which utilized glucose. Trehalose is mentioned for use in the dialysis system as a disaccharide that will not be readily cleaved to glucose and thus avoid raising the blood glucose level. Trehalose has also been described as suitable for use in parenteral formulations primarily because it can be sterilized by autoclaving without the browning associated with conventional parenteral formulations. Japanese Patent No. 6-70718.

Trehalose is a common component of the human diet and information is available on its metabolism. Following oral ingestion, trehalose is not absorbed intact through the gastrointestinal tract, as only monosaccharides can pass throughout the intestinal epithelium. Ravich and Bayless (1983) *Clin. Gast.* 12:335–356. Trehalose is metabolized by the enzyme trehalase into two molecules of glucose. Sacktor (1968) *Proc. Natl. Acad. Sci. USA* 60:1007–1014. Trehalase is a normal constituent of most mammalian bodies, including humans, and has been identified in human serum, lymphocytes and the liver, but is principally located in the brush border of the intestinal tract and the renal proximal tubules. Belfiore et al. (1973) *Clin. Chem.* 19:447–452; Eze (1989) *Biochem. Genet.* 27:487–495; Yoshida et al. (1993) *Clin. Chim. Acta* 215:123–124; and Kramers and Catovsky (1978) *Brit. J. Haematol.* 38:4453–461. Trehalase is a membrane bound protein of the human and animal intestinal tract. Bergoz et al. (1981) *Digestion* 22:108–112; Riby and Galand (1985) *Comp. Biochem. Physiol.* 82B:821–827; and Chen et al. (1987) *Biochem. J.* 247:715–724.

All references cited herein are hereby incorporated herein by reference.

DISCLOSURE OF THE INVENTION

The invention relates to methods of sterilizing products, particularly therapeutic products, derived from biological sources and the compositions obtained thereby. The methods include drying the product in the presence of an amount of trehalose sufficient to render heat stability to the product and exposing the dried sample to heating conditions at a temperature and for a duration sufficient to substantially inactivate viruses. Preferably, the heating conditions are sufficient to inactivate non-lipid encapsulated viruses. The drying methods are any known in the art including both ambient drying conditions, including spray and vacuum drying, and lyophilization. The heating conditions cover a wide range of temperatures and heating time combinations.

The invention further encompasses the compositions obtained by the methods. These compositions contain stable biological products and do not contain detectable infectious virus, particularly parvovirus.

BEST MODE FOR CARRYING OUT THE INVENTION

As described in detail herein, there are numerous methods of terminal sterilization of blood-derived biological products. These methods are well known in the art, as exemplified by the references cited herein, and need not be described in detail. Although stringent purification methods such as antibody-affinity chromatography may result in virus-free biological products, none of the commercially feasible methods has been found to consistently render the products free of infectious viruses, particularly non-lipid-encapsulated viruses. In addition, increasing the severity of the sterilization conditions in order to render a product free of infectious viruses, has the drawbacks of diminishing the activity and/or increasing the immunogenicity of the product.

In addition to blood derived products, there are numerous biologically active products that can benefit from the sterilization methods provided herein. These include, but are not limited to, recombinantly produced proteins, native isolated proteins, antibodies, enzymes, cytokines and growth factors, as well as pharmaceutically active molecules such as analgesics, anesthetics, anti-emetics, antibiotics, chemotherapeutic agents, hormones, vitamins and steroids.

Also suitable for use in the claimed methods are any substance that is to be aseptically introduced into an individual. These include, but are not limited to, drugs, antibiotics, imaging agents and diagnostic reagents. Importantly, in the case where the product to be administered is labile, such as cephalosporins, therapeutic antibodies and erythropoietin, the invention provides stable, dried, sterile compositions that can be rehydrated just prior to use. Trehalose is well suited for injectable, infusible etc. agents in that it breaks down to two molecules of glucose upon exposure to trehalase in the bloodstream. The glucose may cause a minor, transient increase in blood sugar levels but this is of little clinical concern.

The present invention encompasses methods of terminal sterilization of products that need to be administered aseptically to an individual. The steps of the method include obtaining a dried sample containing the product and an amount of α-D-glucopyranosyl-α-D-glucopyranoside (trehalose) sufficient to render substantial heat stability to the product; and heating the dried sample at a temperature and for a duration sufficient to substantially inactivate viruses, preferably under heating conditions that inactivate non-lipid encapsulated viruses. The dried sample may further contain suitable buffers, adjuvants, etc., preferably in an amount that yields a suitable concentration upon rehydration.

The product can be derived from a variety of sources. Preferably, the products are derived from any known biological source, including, but not limited to, blood, plasma, serum, placenta, milk, urine, cell cultures, and cell culture supernatant. Additionally, the product can be derived synthetically, either by chemical or enzymatic syntheses or by the use of recombinant DNA techniques. Methods of preparation of these sources and methods of isolation of the products are well known in the art.

Typically, products isolated or derived from blood, plasma and serum, include, but are not limited to, albumin products, immune globulins, coagulation products, and protease inhibitors. Albumin products include, but are not limited to, HSA, cold insoluble globulins and fibrinogen. Immune globulins include, but are not limited to, antibodies against tetanus, pertussis, hepatitis B, Rho (D), varicella zoster, and rabies. Coagulation products include, but are not limited to, antihemophilic factor VIII, factor IX complex, and activated factor IX complex. Protease inhibitors include, but are not limited to, $\alpha$-1 protease inhibitor, $\alpha$-1 antitrypsin and antithrombin III. Other sources of these products are available, for instance, albumin can be obtained from placental sources.

Where the biological source is cell culture or cell culture supernatant the products include, but are not limited to, colony stimulating factors, monoclonal antibodies and derivatives thereof, and growth factors. Typical growth factors include, but are not limited to, both naturally derived and recombinant erythropoietin, cytokines and interleukins.

Where the product is an agent that needs to be aseptically administered, the products include, but are not limited to, analgesics, anesthetics, chemotherapeutic agents, hormones and vaccines. Analgesics include, but are not limited to, morphine, benzocaine, pethidine, and Demerol™ (meperidine), anesthetics include, but are not limited to, bupivacaine, atracurium and vecuronium.

Chemotherapeutic agents include, but are not limited to, radioisotopes, vinca alkaloids such as the vinblastine, vincristine and vindesine sulfates, adriamycin™ (doxorubicin hydrochloride), bleomycin sulfate, Carboplatin, cisplatin, cyclophosphamide, Cytarabine, Dacarbazine, Dactinomycin, Duanorubicin hydrochloride, Doxorubicin hydrochloride, Etoposide, fluorouracil, mechlororethamine hydrochloride, melphalan, mercaptopurine, methotrexate, mitomycin, mitotane, pentostatin, pipobroman, procarbaze hydrochloride, streptozotocin, Taxol™ (paclitaxel), thioguanine, and uracil mustard.

Suitable hormones include, but are not limited to estrogen, testosterone, progesterone and synthetic analogs thereof. Typical vaccines include, both single and multiple antigen subunit vaccines as well as killed bacterial and viral preparations and cancer antigens. Typical antibiotics include, but are not limited to, cephalosporins and aminoglycosides.

The method includes a first step of obtaining a dried sample. A variety of methods may be utilized to dry the sample. These include, but are not limited to, air drying, vacuum drying, spray drying and freeze drying. These methods are exemplified in detail in the examples presented herein and are well known in the art. See, e.g. U.S. Pat. Nos. 4,891,319; 5,026,566; and 5,149,653.

The samples are typically prepared in solution or suspension and include the product, a sufficient amount of trehalose to render heat stability to the product, and any other typical additive such as suitable buffers, adjuvants, etc. Typically, trehalose is present in an amount of 1–50% by weight of the solution. However, the trehalose can be more dilute or concentrated. If less dilute, drying times may be prohibitive, and, if more concentrated, the solution may become viscous. The exact initial concentrations of product, trehalose and any additive will need to be determined empirically, but this is well within the skill of one in the art given the examples provided herein. Preferably, the concentration of product and trehalose is such that after drying less than about 30% loss of activity of the product occurs. More preferably, there is less than 15% loss of activity and most preferably, there is less than 10% loss.

Once the dried sample has been obtained it is subject to heating conditions at a temperature and duration sufficient to inactivate viruses. Typically, the dried sample is subject to heating at 80° C. for 72 hours to inactivate lipid encapsulated viruses and 90° C. for 72 hours to further inactivate non-lipid encapsulated viruses. The optimal combination of heat and duration of heating will be determined empirically. Such a determination is within the skill of one in the art given the examples provided herein. Typically, the optimal conditions are determined by spiking a test sample with either the virus to be inactivated or a virus having similar physical characteristics. Typically, a loss of four $\log_{10}$ titre of the spiked virus is considered to be "inactivation" as a 4 $\log_{10}$ drop in titre is the regulatory authority requirement for viral inactivation/removal procedure.

The method results in substantial heat stability of the product. Preferably, the method results in less than about a 30% loss in activity of the product. More preferably, the method results in less than about 15% loss in activity of the product. Most preferably, the method results in less than about 10% loss in activity of the product.

The method provides dried samples of high stability and capable of being stored for long periods of time. This storage stability is related to the residual moisture of the sterilized product. Preferably, the method produces a dried sample having a residual moisture content of less than about 4%. More preferably, the residual moisture content is less than about 2%. Most preferably, the residual moisture content is about 0.8–1.0%. Residual moisture can be measured by a variety of methods, including, but not limited to, differential thermal analysis, thermogravimetric methods or Karl Fisher coulometric titration.

The range of heating temperature and times varies widely, the optimum time for a particular sample can be determined empirically given the knowledge in the field and the examples provided herein. The results presented herein indicate that heating at about 80° C. for about 72 hours is effective, as is heating at 90° C. for about 20 hours. Longer time periods and/or higher temperatures may be utilized with potential concomitant loss in product activity.

Preferably, the method results in a four $\log_{10}$ fold reduction in infectivity of the contaminating viruses. A number of methods are known for making this determination. Many of these are cited above and a number of others are known in the art. As lipid encapsulated viruses are less resistant to heat treatment than non-lipid encapsulated viruses, a determination of the loss of infectiousness of a non-lipid encapsulated virus indicates that all lipid encapsulated viruses have also been inactivated. The non-lipid encapsulated viruses include, but are not limited to, hepatitis A virus and parvoviruses. Preferably, the non-lipid encapsulated virus is parvovirus.

The invention also encompasses compositions obtained by the methods of the claimed invention. The compositions are free of detectable infective viruses and are extremely storage stable. In addition, the reduced denaturation or chemical degradation of therapeutic products during processing results in a decrease in the incidence of immune reactions to recipients of the products.

The compositions are preferably in single dosage form, especially for drugs such as analgesics and chemotherapeutics. Single dosage forms can be produced by aliquoting the initial solution or suspension into suitable containers and processing the containers separately. Preferably, such aliquoting and processing is automated. Alternatively, the material can be processed in batches of more than one dose and the dried product can be divided into single doses. The invention thus encompasses single dose forms of the claimed composition.

For products such as HSA, batch-wise processing is preferred. Large batches can be processed to be provided in bulk commercially. The invention thus further encompasses bulk forms of the claimed composition.

The following examples are provided to illustrate, but not limit, the claimed invention.

EXAMPLE 1

Comparison of Effect of Different Sugars on Parvovirus Infectivity and Alkaline Phosphatase Activity A stock solution of 1 mg/ml alkaline phosphatase in a 50% trehalose solution made up in 25 mM HEPES buffer containing 50 mM ammonium bicarbonate and 2% HSA was spiked with $10^{6.5}$ TCID 50/ml canine parvovirus. 250 $\mu$l aliquots of the spiked formulation were either vacuum dried or freeze dried in 3 ml Wheaton glass pharmaceutical vials using an FTS drier or Labconco freeze drier.

For vacuum drying, the shelf temperature was initially set at 30° C. while the vacuum was reduced in a stepwise fashion to 30 mTorr, when the shelf temperature was increased to 60° C. and the drying carried out for a further 12–16 hrs. For freeze drying, the samples were frozen by reducing the shelf temperature to −40° C. at 5° C. per minute and the vials were allowed to freeze completely for 1 hour before the vacuum was reduced 10 mTorr and the samples dried at −40° C. for 40 hours. The shelf temperature was then raised to +20° C. at 0.05° C. per minute and samples dried at +20° C. for 3 hours and finally the shelf temperature was raised to +40° C. at 0.05° C. per minute and samples dried at +40° C. for a further 2 hours. Vials were stoppered under vacuum and samples were kept at 4° C. as dried controls. For terminal sterilization, vials were treated at 80° C. for 72 hours or 90° C. for 20 hours in an Heraeus drying oven. $Log_{10}$ reduction in parvovirus activity and % reduction in alkaline phophatase activity were evaluated.

Parvovirus was assayed by titration on cell culture and the endpoint was determined by agglutination of porcine red blood cells. Briefly, dried samples were reconstituted in their original volume using sterile distilled water and a tenfold dilution series prepared in Eagles Minimum Essential Maintenance culture media (EMEM). A suspension of A72 cells in EMEM containing 5% fetal bovine serum was prepared by trypsinisation of a confluent flask of cells and a 1 ml of cell suspension containing 2–5×$10^3$ cells/ml was aliquoted into the wells of a 24 well cell culture plate. 100 $\mu$l of each dilution of viral sample was inoculated into four replicate wells of the cell culture plate and the plates incubated for 14 days at 37° C. in an atmosphere of 5% $CO_2$.

After 14 days, cell culture medium from each well was tested for hemagglutinin activity using 1% porcine red blood cells. Viral titre as $log_{10}$ TCID 50/ml was calculated using the Karber formula for quantitation of the end point in virus infectivity assays, namely Karber formula=−log of dilution interval−(sum of positive tests)−0.5.

Alkaline phosphatase was assayed colorometrically, using the commercial reagent, Sigma fast™ alkaline phosphatase substrate assay. Briefly, a doubling dilution series was prepared for the samples and a standard alkaline phosphatase preparation (1 mg/ml) and 100 $\mu$l of substrate was added to 100 $\mu$l of sample in an EIA plate and incubated in the dark for 30 minutes. Color development was read at 405 nm using a titertek multiscan interfaced with a delta soft plate reader package and the activity of the samples was calculated from absorbance values corresponding to the linear section of the standard curve. Dried controls were assigned 100% activity and % reduction in activity of the treated samples were calculated from these values.

For all virus assays, $log_{10}$ reduction in titre of the treated samples was calculated by subtraction of $log_{10}$ TCID 50 virus recovered from the $log_{10}$ TCID 50/ml values of the dried controls. Results are shown in Table 1. In Table 1, ≧means that the virus was below the detection level of the assay, RIT means "reduction in titer" HSA stands for human serum albumin, * means $log_{10}$ TCID 50/ml parvovirus in dried control=6.5, ** means alkaline phosphatase activity in dried control=100%, GPS stands for glucopyranosyl sorbitol, and n.d. stands for not done. The abbreviations are the same, throughout the examples section and in the tables.

TABLE 1

| | $Log_{10}$ reduction in parvovirus titre, % reduction in alkaline phosphatase activity after terminal sterilization at 90° C. for 20 hours | | | |
|---|---|---|---|---|
| | freeze dried | | vacuum dried | |
| Sample | $Log_{10}$ RIT parvovirus * | % alk'phos' reduction ** | $Log_{10}$ RIT parvovirus * | % alk'phos' reduction ** |
| trehalose | ≧4.4 | 7.0 | ≧4.0 | 0 |
| trehalose + HSA | ≧4.4 | 9.5 | ≧4.0 | 0 |
| sucrose | ≧4.4 | 65 | ≧4.0 | 48 |
| sucrose + HSA | ≧4.4 | 68 | ≧4.0 | 56 |
| lactitol + HSA | ≧5.6 | ≧99 | n.d. | n.d. |
| lactose + HSA | ≧5.0 | 44 | n.d. | n.d. |
| sorbitol | ≧4.0 | ≧99 | n.d. | n.d. |
| sorbitol + HSA | ≧4.0 | ≧99 | n.d. | n.d. |
| GPS | ≧4.0 | ≧99 | n.d. | n.d. |
| GPS + HSA | ≧4.0 | ≧99 | n.d. | n.d. |

EXAMPLE 2

Terminal Sterilization to Eliminate Parvovirus Infectivity Without Loss of Biological Activity by Vacuum Drying in Trehalose; Effect of Temperature and Time A stock solution of 1 mg/ml alkaline phosphatase in a 50% trehalose solution made up in 25 mM HEPES buffer containing 50 mM ammonium bicarbonate and 2% HSA was spiked with $10^{6.5}$ TCID 50/ml canine parvovirus and dried under vacuum in an FTS drier. 250 $\mu$l of formulation was dried in 3 ml vials in FTS drier using a manual programme which achieved final operating parameters of 30 mTorr vacuum and 60° C. shelf temperature. Vials were stoppered under vacuum and samples were kept at 4° C. as dried controls.

For terminal sterilization, vials were treated at 80° C. for 72 hours or 90° C. for up to 144 hours in an Heraeus drying oven. $Log_{10}$ reduction in parvovirus activity and % reduction in alkaline phophatase activity were evaluated. Parvovirus was assayed by titration in cell culture followed by agglutination of porcine red blood cells as described in Example 1. Viral titre as $log_{10}$ TCID 50/ml was calculated using the Karber formula as described in Example 1. Alkaline phosphatase was assayed colorometrically, using the commercial reagent, Sigma fast™ alkaline phosphatase substrate assay as in Example 1.

A summary of the results obtained are shown in Table 2 which depicts the $log_{10}$ reduction in parvovirus titre and % reduction in alkaline phosphatase activity following terminal sterilization at 80° C. for 72 hours or 90° C. for 144 hours. In Table 2, * stands for $log_{10}$ TCID 50/ml parvovirus in dried control=6.5 ** stands for the activity of alkaline phosphatase in dried control=100% and ≧stands for below the detection limit of the assay.

TABLE 2

| Treatment | $Log_{10}$ reduction in parvovirus titre * | % reduction in alkaline phosphatase activity ** |
|---|---|---|
| 80° C./72 hours | 3.0 | 0 |
| 90° C./20 hours | 3.0 | 0 |
| 90° C./24 hours | 4.4 | 0 |
| 90° C./48 hours | ≧5.0 | 0.8 |
| 90° C./72 hours | ≧5.0 | 0 |
| 90° C./96 hours | ≧5.0 | 3.3 |
| 90° C./120 hours | ≧5.0 | 0 |
| 90° C./144 hours | ≧5.0 | 3.4 |

EXAMPLE 3

Terminal Sterilization to Eliminate Enveloped and Non-enveloped Virus Infectivity Without Loss of Biological Activity by Vacuum Drying in Trehalose In this experiment, the same formulations as in Example 1 were spiked with three different virus preparations: poliovirus; parvovirus (non-enveloped RNA and DNA containing viruses respectively); and measles virus (enveloped RNA virus). $Log_{10}$ reduction in virus titre and % reduction in alkaline phosphatase activity were evaluated as described previously or below. Poliovirus was assayed using a cell cytopathic assay. Briefly, dried samples were reconstituted in their original volume using sterile distilled water and a tenfold dilution series prepared in EMEM and 100 μl dilutions were inoculated into five replicate wells of a 96 well cell culture plate containing a confluent monolayer of Vero cells. The plates were incubated for 7 days and virus induced cytopathic effect scored by inspection of the wells using light microscopy. Viral titre, as $log_{10}$ TCID 50/ml virus recovered, was again calculated using the Karber formula for quantitation of the end point in virus infectivity assays. For all virus assays, $log_{10}$ reduction in titre of the treated samples was calculated by subtraction of $log_{10}$ TCID 50/ml virus recovered from the $log_{10}$ TCID 50/ml values of the dried controls.

Measles virus infectivity was determined using a plaque assay. Briefly, dried samples were reconstituted in their original volume using sterile distilled water and a tenfold dilution series prepared in EMEM. 200 μl of each dilution was inoculated into duplicate wells of a 6 well plate containing a confluent monolayer of Vero cells. After virus adsorption to the cells for 1 hour at 37° C., 2 ml of overlay medium (EMEM containing 1% carboxymethyl cellulose and 5% foetal bovine serum) was added to each well. The plates were then incubated for 7 days at 37° C. in an atmosphere of 5% $CO_2$. Virus-induced by plaque formation in cell monolayers was visualized by Crystal violet staining.

Plaques were counted and virus recovered was quantified by calculation of plaque forming units per ml, namely PFU/ml=number of plaques×dilution factor×5. For all virus assays, $log_{10}$ reduction in titre of the treated samples was calculated by subtraction of $log_{10}$ PFU/ml virus recovered from the $log_{10}$ PFU/ml values of the dried controls. The results obtained are presented in Table 3 which shows the $log_{10}$ reduction in poliovirus, measles virus and parvovirus titre and % reduction in alkaline phosphatase activity following terminal sterilization at 80° C. for 72 hours or 90° C. for 20 hours. In Table 3, * stands for $log_{10}$ TCID 50/ml poliovirus in dried control=4.5;  stands for $log_{10}$ PFU/ml measles virus in dried control=5.10; * stands for $log_{10}$ TCID 50/ml parvovirus in dried control=6.5; **** stands for the activity of alkaline phosphatase in dried control=100%; and ≧stands for below the detection limit of the assay.

TABLE 3

| | $Log_{10}$ Reduction in virus titre | | | Reduction |
|---|---|---|---|---|
| Treatment | Poliovirus * | Measles virus ** | Parvovirus *** | in alk phos activity (%) **** |
| 80° C./72 hours | ≧3.0 | ≧4.1 | ≧4.0 | 0–3 |
| 90° C./20 hours | ≧3.0 | ≧4.1 | ≧4.0 | 0–5 |

EXAMPLE 4

Terminal Sterilization to Eliminate Parvovirus from Blood Product Without Loss of Biological Activity by Driving in Trehalose Fibrinogen (Fraction 1, Type 1-S, Sigma Chemical company) was dissolved in 10% and 25% solutions of either trehalose or sucrose containing 10% sodium citrate and 15% sodium chloride and the solutions centrifuged to remove any insoluble material and the protein concentrations adjusted to a final fibrinogen concentration of 5 mg/ml. The stock fibrinogen solutions were was spiked with $10^{6.5}$ TCID 50/ml canine parvovirus and 12 ml aliquots of the fibrinogen solution were dispensed into 5 ml Wheaton pharmaceutical glass vials and the samples vacuum dried in an FTS drier or freeze dried in a Labconco freeze-drier. For vacuum drying, the drier shelves were pre-cooled to 10° C. and vacuum reduced to 30,000 mTorr. The shelf temperature was then raised to 40° C. and the vacuum reduced to 30,000, Torr for 2 minutes, 20,000 mTorr for 2 minutes and 10,000 mTorr for 20 minutes. The vacuum was then raised to 30,000 mTorr for 5 minutes and then reduced to 30 mTorr and the samples dried overnight at a shelf temperature of 60° C. For freeze drying, the samples were frozen at 5° C./min to −40° C., held at −40° C. for 16 hours and then the shelf temperature was raised to −35° C. and the samples dried at a vacuum of 10 mTorr for 80 hours. The shelf temperature was raised to 25° C. and the samples dried at a vacuum of 10 mTorr for a further 5 hours. All the vials were sealed under vacuum and samples to be terminally sterilized were heat sterilized by heating in a Heraeus oven at 90° C. for 20 or 48 hours.

Vials were reconstituted and total soluble protein and clottable protein determined. The clotting assay for fibrinogen was a modification of the National Institute of Biological Standards thrombin clotting assay. Briefly, fibrinogen samples and standards were clotted by addition of thrombin to the fibrinogen solution and the protein concentration in the clot measured by solubilisation of the clot in 7M urea and quantitating the absorbance at 280 nm.

Upon addition of 3 ml of water, all preparations reconstituted readily apart from the fibrinogen/sucrose preparations that had been exposed to 90° C./20 hours. The freeze dried fibrinogen/sucrose preparations that had been exposed to 90° C./20 hours showed a distinct brown coloration. The protein assays showed that most of the protein had dissolved upon reconstitution, (~90%), except in the case of the fibrinogen/sucrose 90° C./20 hour vials which showed very little soluble protein. The clotting assays showed that of the soluble protein, ~95% clotted upon addition of thrombin. A summary of the results obtained are shown in Table 4 which depicts Clottable fibrinogen and $\log_{10}$ reduction in parvovirus titre.

TABLE 4

|  | 80° C./72 hours | | 90° C./20 hours | |
| --- | --- | --- | --- | --- |
|  | % clottable | log. loss | % clottable | log. loss |
| Trehalose | | | | |
| Freeze dried | 87 | ≧4 | 83 | 4.0 |
| Vacuum dried | 94 | ≧3.75 | 89 | 3.75 |
| Sucrose | | | | |
| Freeze dried | 0 | ≧5 | 44 | ≧5.0 |
| Vacuum dried | 68 | ≧4.75 | 43 | ≧4.75 |

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention, which is delineated by the appended claims.

What is claimed is:

1. A method of terminal sterilization of a biologically active product suitable for sterile administration to an individual comprising:
   (a) providing a dried sample comprising the biologically active product, wherein the product is fibrinogen, and an amount of α-D-glucopyranosyl-α-D-glucopyranoside sufficient to render heat stability to the product; and
   (b) heating the dried sample at a temperature and for a duration sufficient to inactivate parvovirus.

2. The method according to claim 1, wherein the biologically active product is obtained from a biological source selected from the group consisting of blood, plasma, serum, cell culture, and cell culture supernatant.

3. The method according to claim 2, wherein the biological source is cell culture or cell culture supernatant and the product is recombinant.

4. The method according to claim 1, wherein the dried sample is obtained by the method selected from the group consisting of air drying, vacuum drying, spray drying and freeze drying.

5. The method according to claim 1, wherein the heating step results in less than about a 30% loss in activity of the product.

6. The method according to claim 5, wherein the heating step results in less than about a 15% loss in activity of the product.

7. The method according to claim 6, wherein the heating step results in less than about a 10% loss in activity of the product.

8. The method according to claim 1, wherein the dried sample has a residual moisture content of less than about 4%.

9. The method according to claim 8, wherein the residual moisture content is less than about 2%.

10. The method according to claim 9, wherein the residual moisture content is less than about 1%.

11. The method according to claim 1, wherein the heating temperature is about 80° C. and the duration of heating is about at least 72 hours.

12. The method according to claim 1, wherein the heating temperature is about 90° C. and the duration of heating is about at least 20 hours.

13. The method according to claim 1, wherein inactivation of parvovirus results in about $10^4$-fold reduction in infectivity of the virus.

14. A composition comprising a terminally sterilized biologically active product suitable for sterile administration to an individual, wherein the product is fibrinogen, and further wherein the product is prepared by heating a dried sample comprising the biologically active product and an amount of α-D-glucopyranosyl-α-D-glucopyranoside sufficient to render heat stability to the product, at a temperature and for a duration sufficient to inactivate parvovirus.

15. The composition according to claim 14, wherein the biologically active product is obtained from a biological source selected from the group consisting of blood, plasma, serum, cell culture, and cell culture supernatant.

16. The composition according to claim 15, wherein the biological source is cell culture or cell culture supernatant and the product is recombinant.

17. The composition according to claim 14, wherein the dried sample is obtained by the composition selected from the group consisting of air drying, vacuum drying, spray drying and freeze drying.

18. The composition according to claim 14, wherein the heating step results in less than about a 30% loss in activity of the product.

19. The composition according to claim 18, wherein the heating step results in less than about a 15% loss in activity of the product.

20. The composition according to claim 19, wherein the heating step results in less than about a 10% loss in activity of the product.

21. The composition according to claim 14, wherein the dried sample has a residual moisture content of less than about 4%.

22. The composition according to claim 21, wherein the residual moisture content is less than about 2%.

23. The composition according to claim 22, wherein the residual moisture content is less than about 1%.

24. The composition according to claim 14, wherein the heating temperature is about 80° C. and the duration of heating is about at least 72 hours.

25. The composition according to claim 14, wherein the heating temperature is about 90° C. and the duration of heating is about at least 20 hours.

26. The composition according to claim 14, wherein inactivation of parvovirus results in about $10^4$-fold reduction in infectivity of the virus.

* * * * *